US008473908B2

(12) United States Patent
Canda et al.

(10) Patent No.: US 8,473,908 B2
(45) Date of Patent: Jun. 25, 2013

(54) ADMINISTRATION OF DIFFERENTLY-VERSIONED CONFIGURATION FILES OF A MEDICAL FACILITY

(75) Inventors: Valer Canda, Erlangen (DE); Stefan Thesen, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 1592 days.

(21) Appl. No.: 11/774,895

(22) Filed: Jul. 9, 2007

(65) Prior Publication Data

US 2008/0033753 A1 Feb. 7, 2008

(30) Foreign Application Priority Data

Aug. 4, 2006 (DE) .......................... 10 2006 036 584

(51) Int. Cl.
*G06F 9/44* (2006.01)
(52) U.S. Cl.
USPC .......................................................... 717/121
(58) Field of Classification Search
USPC .......... 717/102, 101, 124, 120–123; 715/229, 715/744; 705/3, 35, 37, 319; 709/203, 223, 709/201; 726/27; 707/100, 204; 713/166
See application file for complete search history.

(56) References Cited

U.S. PATENT DOCUMENTS

| 7,124,101 | B1 * | 10/2006 | Mikurak .......................... 705/35 |
| 2003/0074302 | A1 * | 4/2003 | Cope ................................ 705/37 |
| 2003/0182652 | A1 * | 9/2003 | Custodio ....................... 717/122 |
| 2004/0215646 | A1 * | 10/2004 | Kaler et al. ................... 707/100 |
| 2005/0027757 | A1 * | 2/2005 | Kiessig et al. ................ 707/204 |
| 2006/0069717 | A1 * | 3/2006 | Mamou et al. ................ 709/203 |
| 2007/0061266 | A1 * | 3/2007 | Moore et al. .................... 705/51 |

FOREIGN PATENT DOCUMENTS

EP 1 312 031 B1 4/2006

OTHER PUBLICATIONS

"Oracle Network Manager Administrator's Guide," (2006).

* cited by examiner

*Primary Examiner* — Tuan A Vu
(74) *Attorney, Agent, or Firm* — Schiff Hardin LLP

(57) ABSTRACT

In a method, system and computer program product for administration of different versions of a configuration file for configuration of medical apparatuses in a clinical system, the configuration file can also be locally changed at the apparatus itself and be made centrally available. Together with one configuration file, a set of versions regarding the configuration file is automatically administered while maintaining consistency of the data.

11 Claims, 1 Drawing Sheet

ADMINISTRATION OF DIFFERENTLY-VERSIONED CONFIGURATION FILES OF A MEDICAL FACILITY

BACKGROUND OF THE INVENTION

1. Field of the Invention

The present invention is in the field of medical process control and in particular concerns a method, a system and a product for administration of variable configuration files in a medical facility.

2. Description of the Prior Art

A number of apparatuses that are designed for execution of examinations, measurements and/or for acquisition of image data, etc. are normally provided in a medical facility such as, for example, in a hospital or a special clinic. These apparatuses are normally connected to a network and thus are involved in data exchange. Moreover, there are a number of processes that are designed for execution of workflows or for execution of other medical procedures.

It is common to medical-technical apparatuses as well as to the medical-technical processes that they must be defined, specified and executed in a specific form and thus are fixed. For each apparatus and/or for each process there are thus metadata that are necessary for execution of the respective process or for startup of the respective apparatus. The metadata are data that can be relevant in connection with the apparatus and/or with the respective process, for example specification of the measurement procedures that must be implemented for acquisition of specific image data or specific settings that must be effected on the apparatus, etc. The metadata are typically stored in standardized protocols. Depending on the modality (MR, CT, PET, etc.) there are different configuration files or, respectively, different measurement protocols that must be changed from time to time in the event that, for example, a modification of an already-existing configuration file is required based on a long-term study conducted by the hospital or clinic.

The respective configuration files could previously be only locally administered and modified and only manually forwarded to other apparatuses and/or units in the clinical facility. This previous procedure is deficient since significant errors could arise by a valid configuration file being overwritten by an unauthorized change so that the previous data of the configuration file are then no longer available.

Previously only local and manual changes to the respective configuration file could be effected without the configuration files having been centrally administered. A configuration file, for example a specific measurement protocol, thus could be altered by a physician at one point in time without his or her colleagues having been automatically informed about this. The colleagues then unknowingly use the changed protocol at a later point in time although it is unsuitable for this application case and possibly results in false or incorrect measurements. Changing a configuration file was previously disadvantageously an unregulated and unstructured procedure, such that changes normally remain untrackable and non-transparent.

SUMMARY OF THE INVENTION

An object of the present is to provide for central administration of configuration files that can exist in different versions in a simplified and improved manner.

In a preferred embodiment, this object is achieved by a method for administration of configuration files in a medical facility, wherein the administration encompasses all changes with regard to the configuration file; the configuration file encompasses configurations of processes and/or of apparatuses of the medical facility. The configuration file can exist in different versions. A set of system parameters is associated with each version of the configuration file.

Optionally an authorization to change the configuration file is checked. The configuration file is changed while maintaining the consistency of the data. The changed configuration file is made available for all or selected apparatuses and/or processes. The changed configuration file is stored, such as at a central facility.

The "administration" of configuration files includes definition, application, provision, modification, making available for retrieval, storage, authorization check, access control, checking in, checking out, commenting, versioning, combining (or merging), release and/or other actions with regard to the configuration file.

The medical facility is typically a clinical facility, a hospital or a separate department within a hospital or another medical clinic.

A configuration file contains metadata with regard to the execution of medical-technical processes and/or the operation of medical-technical apparatuses of the medical facility. An example is workflow definitions that, among other things, define a sequence of steps to be executed in the framework of a medical-technical examination or another medical process or parameters with regard to the respective medical-technical apparatus, such as, for example, descriptions, definitions, environmental parameters or other requirements for operation of the respective apparatus, or for execution of the respective process. A configuration can be, for example, a defined measurement protocol, a specification of a measurement process, a post-processing workflow, etc.

A configuration file typically exists in different versions. For example, a first version of a configuration file A can be provided for an ultrasound apparatus of an older version while a second version of the same configuration file A should be used for a newer ultrasound apparatus. The different versions of the configuration file concern the respective application case, environmental parameters, the apparatus, the process and/or system parameters.

The system parameters are normally all quantities or parameters that can have an influence on the respective configuration file. The system parameters thus can be the type of the respective apparatus, the application case, the computation power, the apparatus or, respectively, the apparatus class, the user, the authorization of the user, the operating system, time-related aspects and/or other quantities. A version of a configuration file always concerns different sets of system parameters. In other words, the respective system parameters differ in terms of content from version to version in one and the same configuration file.

The checking of an authorization to execute the respective change includes checking the authorization of the respective user, the apparatus or the process that is affected by the configuration file and/or other authorization checks.

The term "changing" a configuration file is broadly used in the sense of this invention and comprises any changes that are relevant in regard to the configuration file such as, for example, a deletion, a re-application of a configuration file and a changing of a pre-existing configuration file. The effect of the respective change of the configuration file can be different. It can thus be set that a local change of a configuration file should, for example, also be valid only locally, while other configuration files should apply at other apparatuses. As an alternative to this, it is possible that, given a local change to a configuration file, this should also be provided centrally and thus also should be used by all other apparatuses. In a preferred embodiment of the invention not only must the respective change be input, but also it must additionally be specified to what extent this change should be applicable (for example for which apparatuses and/or for which processes).

A significant goal of the inventive solution is that any changes with regard to the respective configuration file are transparent and trackable. Moreover, a central administration of the respective configuration file should be enabled in all versions. Therefore, normally in principle all changes with regard to the configuration file are detected and also stored. However, in specific exceptional situations a change to the configuration file that has, for example, only been generated for a limited time span for testing purposes, is not stored. However, it is typically set that all configuration file changes are stored so that it is ensured that individual changes can be tracked and possibly also reversed.

In contrast to conventional procedures that merely provided a locally limited, autonomous administration of configuration files, according to the invention a central configuration file administration is provided. This offers the advantage that changes can in fact be executed locally, at each host, but these changes are centrally administered and checked for consistency. A version management thus can be provided with regard to the respective configuration file.

Particularly with regard to radiological apparatuses and/or radiological processes, it is typical and desired that a configuration file be dynamically and flexibly adapted to the respective application case. It is frequently also desirable to test new configuration files (for example new measurement protocols). Therefore, in a preferred embodiment of the invention, the configuration file can also be locally changed in order, for example, to test a new measurement protocol. This change and possibly the result of the changed measurement protocol are then automatically detected and stored by the system. This approach offers more flexibility with regard to the daily radiological practice in which a physician can perhaps locally and independently bring in protocol changes. Alternatively, however, it is possible for changes with regard to the configuration file can only be executed from a central point (for example by an administrator). Although this procedure represents a limitation and is less flexible, it can be advantageous for highly safety-critical changes or settings. For the average person skilled in the art it is furthermore apparent that hybrids of the two embodiments mentioned in the preceding can also be used, so that a centralized and/or a decentralized change of configuration files are possible.

It is normally provided that, before a change of a configuration file, an authorization for implementation of this change is automatically checked. The scope of the check can be dynamically configured. An authorization of the respective user is typically queried; a check of the respective computer or of the respective user interface, an authorization check of the department that is associated with the respective user; or other check criteria, can be applied. It is thus advantageously possible to be able to securely preclude an unauthorized change with regard to a configuration file. This increases the reliability and security of the entire system.

In a preferred embodiment, a notification signal can be set that is automatically sent to a configurable instance (for example to the administrator) in all or in selected cases in the event that a change to the configuration file has been executed. This increases the transparency and the trackability of changes in the system.

A significant advantage of the inventive solution is that an archiving of all versions ensues with regard to a configuration file. All versions of a configuration file are typically stored or archived and can thus possibly also be used again or repeatedly at a later point in time.

A release of a version of a configuration file inventively ensues dynamically. This means that one from the set of the archived configuration file versions can be selected and validated, which is then, for example, also globally unlocked for all other apparatuses. It likewise lies within the scope of this invention to unlock a specific configuration file version only for a selection of apparatuses. This enables further design leeway and accords the inventive solution a further degree of freedom by allowing apparatuses or processes that should be affected by the respective change to be dynamically regulated. In other words, it can be configured as to which apparatuses or processes the change should be valid and for which it should not.

A further significant aspect of the present invention is that a number of users can work simultaneously on the same configuration file and may change this file. This is possible by a consistency mechanism being automatically provided that ensures that a consistent data retention is provided at every point in time. This is achieved by acquiring a file to be checked out before a planned change. A local copy of a server file is internally stored upon this checkout operation. The local copy is no longer write-protected for the respective user and he or she can arbitrarily alter the file. Moreover, the user can locally test his changes. After the execution of the change, the user can select whether the user discards his or her changes or whether the user would like to archive those changes. In the event that he would like to store his changes, he implements a check-in operation. The changed version of the configuration file is stored on the server. If possible, further attributes can be determined here that specify for which apparatuses or for which processes the changed configuration file should be valid.

In the event that two different users execute changes on the same configuration file that temporally overlap, the user whose check-in operation is chronologically later is informed that he or she has not edited the configuration file in the most current form. A query to the user is then normally automatically generated with which the user is asked whether he or she nevertheless would like to directly check in his or her version, or whether the user would first like to implement a merge process, thus a reconciliation with the respective most current version. The retention of consistency of the data thus advantageously ensues according to the first come, first serve principle.

In principle, all previously checked-in versions of the same configuration file are stored on the server. This can advantageously ensue in the form of a list or a tree structure. It is also possible for the previously-stored versions of a configuration file to be graphically shown in a specific data structure. This advantageously ensues in the form of a version tree, whereby the different versions are shown as nodes and the temporal or hierarchical conditions are shown as connection lines. Further information can additionally be superimposed (for example by whom, which department, which computer, etc. the respective configuration change has been executed). Moreover, it is possible to graphically compare different versions of configuration files and to graphically show the respective differences. This increases the trackability of changes and therewith the transparency of configuration files.

The merge tool mentioned in the preceding moreover embodies the functionality to merge two arbitrary versions of a configuration file. After execution of the merge tool or the merge operator, a graphical display of the respective merge operation can be provided that then contains all configurations of both versions.

The inventive method advantageously has an inheritance or heredity mechanism with regard to the administration of the respective versions of a configuration file. An inheritance relation can be defined between arbitrary nodes of the tree structure mentioned in the preceding. This means that a version is also automatically handed down to other entities (apparatuses or processes) given the existence of such an inheritance relation. An inheritance relation can in principle be defined not only between different apparatuses, processes and/or other entities of the medical facility, but also it can be established between two different files on the server. In this case, if one of the files changes, the inheritance of the change in the other file is automatically suggested to the user. In principle the inheritance relation can be one-way (unidirectional) or bidirectional. In the first case, only one file can inherit while in the second case both files can inherit the respective changes in principle.

Normally comments or further attributes can be defined and stored in addition to the actual change of the configuration file. For example, privileged users (for example a system administrator) thus can set a validation attribute in all or selected versions, this validation attribute being checked upon a later unlocking or, respectively, release of the version. The version is thus released only in the event that the respective validation attribute is set. Typically all comments, attributes and other parameters with regard to a checked-in version can be displayed to every user.

In principle, every user who can execute changes to the configuration file can belong to one or more apparatus classes or process classes. Given a release of a validated configuration file version, the releasing user must specify for which apparatus class or process class the user would like to release this version. In a version tree there can be a maximum of one released version for every apparatus class (or apparatus type) and/or for every process class (process type, for example ultrasound acquisition or CT acquisition).

In addition to the importation (mentioned above) of newer versions in the inventive system and their storage and release for later usages, in the inventive method it is likewise provided that the user is automatically supported in the readout of an optimized and matching version for the respective apparatus or the respective apparatus class.

A set of versions for a respective configuration file is stored in a memory, advantageously in a central memory of the system. In the event that a new apparatus or a new process is now started or the existing configuration should be changed the respective version optimized for the application case is automatically selected from the set of available versions. Priority and fallback rules are typically used to in the selection. The priority rules have highest priority and are additionally evaluated before the respective apparatus class. The user thereby has the possibility to actively control the selection procedure. The fallback rules have a subordinate priority and take hold when no matching version of a configuration file could be found for the respective apparatus after an evaluation of the respective apparatus class. Which version should be selected given a failing correlation of selection parameters is set or configured with a fallback rule.

According to the inventive method, different operations can be executed. These include:
a check-in,
a branching, thus a branching out into defined structures of the version tree,
a commenting,
a validation,
a release and
a check-out of a version.

Rights for these operations can be given to the individual users by the administrator. These rights can be folder-, file- and/or view-specific. In the framework of this invention a view is understood as a mapping of server contents to the files of the respective client via corresponding interfaces. Every view has its own configuration file in which it is specified according to which criteria this mapping ensues. For example, it can be configured here that in principle only images that are not older than one month are shown. The file specified and "mapped" by means of the view configuration appears locally for the respective apparatus or for the respective user.

As already mentioned, the inventive method advantageously supports an automatic and intelligent search in the set of the archived versions of configuration files. The search ensues using configurable search criteria (for example according to the checked-in or released users, according to comments or according to other attributes). However, it is also possible to reference all or selected files from a foreign server and to mirror these (mirroring). The corresponding data in the files are imported from another server via arbitrary network protocols and thus can be integrated into the set of the archived versions. The method can be adaptively adjusted to the respective application case by means of the number of the inventively provided configuration and setting possibilities. For example, it is possible that a specific change to a configuration file should only be used locally. In this case it is configured that the change serves only for private purposes; this can be identified with a corresponding attribute.

The above object is also achieved in accordance with the invention by having a system for administration of configuration files in a medical facility having at least one memory for storage of configuration files that can exist in different versions, whereby respectively one version of the configuration file is associated with a set of system parameters, and whereby a configuration file comprises configurations of medical-technical processes and/or of medical-technical apparatuses in the medical facility. The system further has a number of clients that are fashioned as apparatuses or on which the processes run. At least one central apparatus has a server that is designed for administration of the configuration files with the respective versions. A modification module is designed to check an authorization for a change when applicable, to change the respective configuration file while retaining consistency and to make this change available for configurable clients.

The above object also is achieved in accordance with the invention by a computer-readable medium encoded with a structure that causes a computer to implement the inventive method described above after loading the medium into the computer. Individual modules of the product can be fashioned as software and/or hardware modules.

DESCRIPTION OF THE PREFERRED EMBODIMENTS

A number of medical-technical apparatuses G (such as, for example, ultrasound apparatuses, computed tomography systems, nuclear magnetic resonance apparatuses and the like) as well as other systems that are designed for execution of medical-technical processes, are arranged in a hospital 10. Typically all medical-technical apparatuses G of the medical facility 10 are connected with one another via a network.

Figure 2:
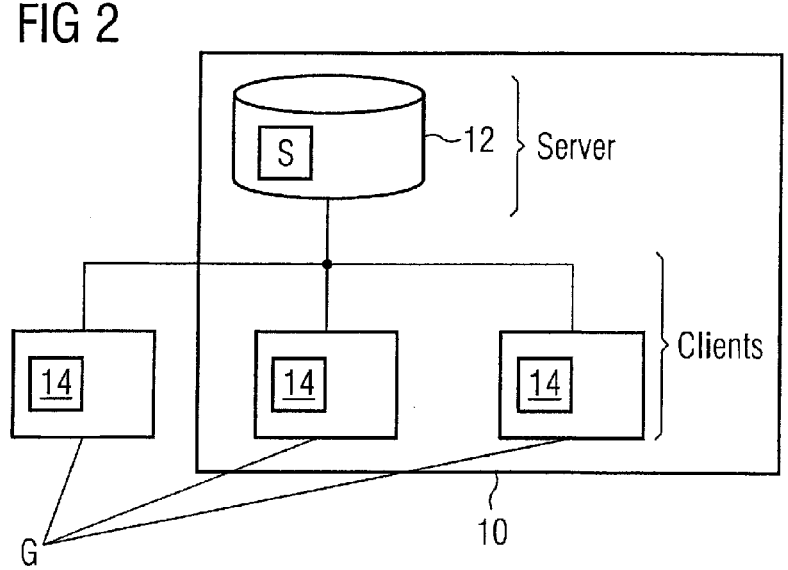
FIG. 2 is an overview representation of units and components according to an embodiment of the invention.

As shown in the manner of an overview in FIG. 2, the inventive system has a central administration entity 12 that has a memory S for storage of configuration files KD with respectively associated versions V.

The inventive system is fashioned as a client-server system, whereby the central administration entity 12 represents the central server that is designed for automatic and central administration of the different configuration files KD with variable versioning. The medical-technical apparatuses G and/or apparatuses that are designed for execution of at least one part of a medical-technical process are fashioned as clients and include a modification module 14. The modification module 14 serves for local processing of the respective configuration file KD and the associated versions V.

A significant advantage of the present invention is that the inventive method enables an automatic administration of different versions V of a respective configuration file KD.

Figure 1:
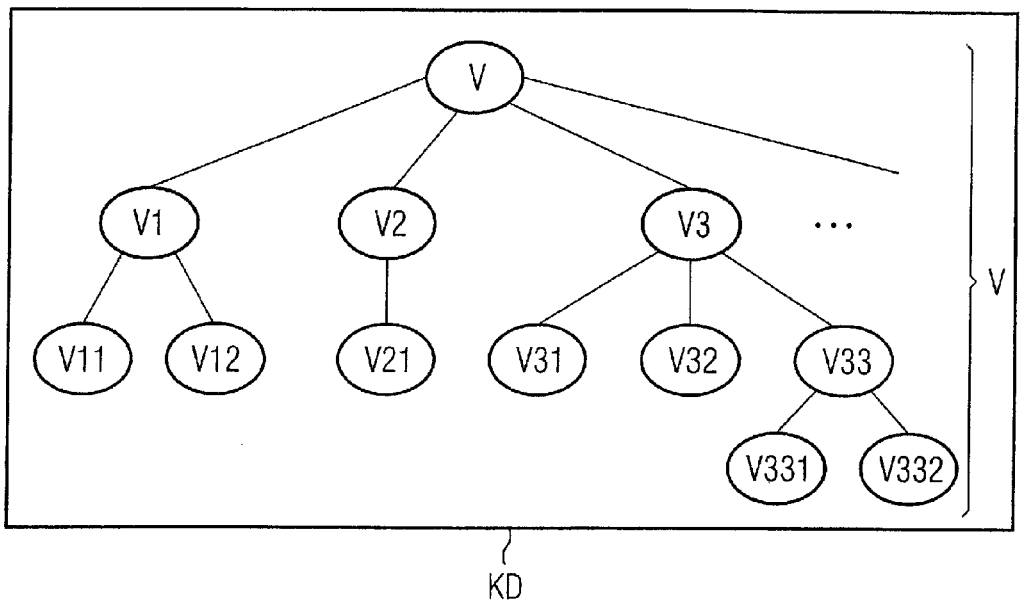
FIG. 1 is an overview representation of a version tree according to an embodiment of the invention.

As schematically shown in FIG. 1, there can be a network of different versions V regarding a respective configuration file KD. All versions V regarding a configuration file KD are stored in a specific data structure. Here this is advantageously a tree-like data structure such as is shown in FIG. 1. The nodes thereby designate the different versions V and the connection line between the node points represents a hierarchical structure between the versions and possibly a temporal sequence for the generation.

In contrast to conventional methods according to the prior art, upon a change of a configuration file KD the preceding version V is no longer overwritten but rather is stored under a different version V. All changes with regard to a configuration file KD can therewith be tracked easily and quickly. Moreover, all changes are transparent and can be undone, if necessary.

The content of the respective configuration file KD is not limited and can pertain, for example, to measurement protocols for different modalities, workflows for image reconstruction programs, scripts and macros (for example fMRI stimulation workflow), etc. The configuration file KD can also include workflow definitions for entire workflows or partial workflows (for example a cardio-examination workflow from the patient registration up to the billing or a measurement program or a measurement protocol or post-processing workflows etc.). Instructions known as "hangings" are likewise included, which are specifications of optimal screen layouts for the execution of a work step. Falling under this category are data with regard to size, position, content of individual screen sections or reports, displayed control elements and available tools. reporting templates thus can be stored in the configuration file KD, such reporting templates serving for description of an examination report and describing possible configurable user interfaces.

The present invention represents a method for automatic administration of such a configuration file KD, wherein the file KD always contains all versions V. Typically a change to the configuration file KD always ensues to a version V of the same configuration file that is then stored under a specific version and can be retrieved again. With the inventive client-server approach and the central administration entity 12, it is possible that changes to the protocol files KD by a number of authorized users (for example physicians) can be implemented and tested on all clients (in particular all clients that have the required information-technological resources, and who are authorized).

For example, if a user would like to change a specific measurement protocol KD, that the user must first check out the corresponding file. During the check-out operation a local copy of the server file KD is internally stored and the local image of this file in view now no longer refers back to the server but rather to a locally hidden copy of the file KD. This file is no longer indicated to the user as write-protected, and the user thus can change it arbitrarily and locally test it. After the alteration and testing the user has the option to discard the changes or to archive those changes. In the first case the configuration file can revert back to the official and central file version on the server by an operation "check-out cancelled" being executed. The local copy is thereby deleted, the mapping to the server is reestablished and the file is displayed as write-protected. In the other case, in the event that the changes should be archived, the user implements a "check-in" operation in which the changed configuration file KD is stored on the server and a corresponding mapping is stored in a view configuration file. There is normally one configuration file KD for each apparatus and/or for each process. It is also possible for a number of configuration files KD to be generated for an apparatus or for a process in order, for example, to be able to satisfy different technological platforms.

In principle, all previously checked-in versions V for each configuration file KD are stored on the server. Depending on the embodiment, the versions can be stored and/or displayed either in the form of a sequential list or in a tree structure. This is schematically shown in FIG. 1. It is possible that a version V has one or more versions derived therefrom in order to make the genesis of the respective versions trackable. Moreover, further details that include metadata in relation to a version change (for example the author, the change date, the description of the changes, the date of check-in processes, etc.) can be stored in a file associated with the respective version V. The version tree typically be can presented graphically.

It is also possible to compare different versions with one another, in particular to compare different versions graphically. For this purpose, a comparison tool is provided in order to graphically emphasize the respective differences.

Moreover, it is possible to establish an inheritance relation between arbitrary branches in the version tree of a configuration file KD. If a new version V is checked in a target branch, it is automatically suggested to the user to implement a combination or a merging of the latest changes into the target branch. Moreover, an inheritance relation can also be defined between two different configuration files KD on the server.

Every client normally belongs to one or more apparatus classes. Privileged users can define the associability of a client with regard to the respective classes (for example "NIH_Cardio", "Avanto_SQ Engine", "Avanto", "1.5 T", "AR_Host" and "Argus_Postprocessing"). Given a release of a validated configuration file KD, the releasing user must specify for which apparatus class the user is releasing this version V. For each apparatus class, there can be at most one released version V in the version tree so that consistent data sets are always employed.

According to the invention also an optimized version V of a configuration file KD, which is optimally suitable for the respective application case or for the respective apparatus and/or process, is automatically selected and determined from the set of the versions V. Specific priority and default rules can be defined for this that establish search criteria according to which the selection is executed.

Moreover, a user can effect specific settings (adjustments) at the apparatus (for example hangings) that in principle should have validity only locally and for which the user intends no release for other users and/or other apparatuses. In this case it is also possible to implement a specific check-in operation, known as a "check-in as private", which is automatically implemented by the inventive method.

Moreover, a further configuration possibility is that specific versions V should be made binding for all or for selected apparatuses (thus, so to speak, a priority version). A privileged user therefore can provide a released version V with a compulsory attribute so that the respective version V is binding for all users or a subject of users and/or for all apparatuses or a subject of apparatuses or apparatus classes, and/or for all processes or a subject of processes, and may not be overwritten with a user-specific priority rule.

However, if no such priority version is present and there are a number of possible versions V, the user is thus supported by an automatic search for an optimally designed version. For example, the search can be executed according to different configurable criteria so that, for example, all measurement protocols are sought that have been checked in after a specific date and are allowed for specific apparatus classes under defined conditions. A tool for safe and consistent administration of different versions V of a configuration file KD in distributed systems thus can be provided.

The modification module 14 in the preferred embodiment is embodied in or at the apparatuses G. Alternatively the modification module 14 need not be fashioned exclusively at the client-side, but can be fashioned client-side and/or server-side.

An important advantage of the inventive solution is that the respective version V of the configuration file KD is in fact locally changed, but is nevertheless centrally administered.

As indicated in FIG. 2, all apparatuses G or clients do not have to directly belong to the medical facility 10. It is also possible for an external client that is engaged in data exchange with the system to be connected to the central administration instance 12. For example, this can be an operator console of an x-ray apparatus in an independent practice associated with the clinical facility 10. The inventive system thus can be expanded quickly and easily.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for administrating configuration files in a medical facility, said medical facility comprising a plurality of computer-operated medical devices that each operate to perform a respective medical task according to a configuration file, a memory in which a plurality of different configuration files, respectively for different medical devices, are stored, at least some of said configuration files being stored in said memory as different versions of a configuration file, and a central administration apparatus in communication with said memory, and being communicable with said medical devices via a network in which said central administration apparatus functions as a server and the medical devices function as respective clients of the server, said method comprising:

prior to implementing a respective medical task at a respective medical device among said plurality of medical devices, establishing a communication connection via said network between the respective medical device and the central administration apparatus to request a configuration file;

in response to the request, automatically initiating a search of said memory at said central administration apparatus, to select a version of a configuration file in said memory that satisfies criteria that include at least appropriateness of a version of a configuration file for use in performing the respective medical task at the respective medical device, and a current run-time environment of the respective medical task at the respective medical device;

automatically making a version of a configuration file in said memory, that satisfies said criteria, available, as a selected configuration file, to the respective medical device for check-out;

from the respective medical device, checking out the selected file, as a checked-out file, from the central administration apparatus via the communication connection in a form that allows a change in the checked-out file to be made at the respective medical device;

after completion of the respective medical task at the respective medical device, returning the checked-out file, via the communication connection, to the central administration apparatus as a checked-in file; and upon receipt of each checked-in file at said central administration apparatus, automatically determining whether the checked-in file contains a change made by the respective medical device and, if a change in the checked-in file is detected, storing the checked-in file in said memory as another version of the configuration file, with an indicator of said change that causes said change to be automatically identified and used by said central administration apparatus, in a subsequent search of said memory initiated by a respective medical device, to satisfy said appropriateness in the criteria of said subsequent search.

2. A method as claimed in claim 1 comprising automatically permitting a configuration file to be checked out only with authorization from said central administration apparatus, and permitting a configuration file to be changed only after the configuration file is successfully checked out with said authorization.

3. A method as claimed in claim 1 comprising automatically transmitting a notification signal to said central administration apparatus from the respective medical device upon execution of a change to a configuration file by the respective medical device.

4. A method as claimed in claim 1 comprising establishing storage of all versions of a configuration file in said memory as a set of stored versions, and generating a release version from said set of stored versions that can be released to a respective medical device in said subsequent search.

5. A method as claimed in claim 1 comprising, via said central administration apparatus, automatically centrally storing every changed configuration file in said memory.

6. A method as claimed in claim 1 comprising, at said central administration apparatus, automatically electronically creating an inheritance mechanism for the respective versions of a configuration file that automatically produces inheritances from one of said versions to another of said versions of said configuration file.

7. A method as claimed in claim 1 comprising allowing a configuration file to be changed in parallel by different medical devices in said plurality of medical devices and automatically ensuring data consistency, at said central administration apparatus, upon check-in of configuration files that were changed in parallel, before permitting said configuration files that were changed in parallel, to be stored in said memory.

8. A method as claimed in claim 1 comprising automatically merging at least two different versions of a configuration file at said central administration apparatus.

9. A method as claimed in claim 1 comprising, from said central administration apparatus, causing display a visual representation of all or selected versions of a configuration file at a respective medical device.

10. A system for administrating configuration files comprising:
 a plurality of computer-operated medical devices at a medical facility that each operate to perform a respective medical task according to a configuration file;
 a memory in which a plurality of different configuration files, respectively for different medical devices, are stored, at least some of said configuration files being stored in said memory as different versions of a configuration file;
 a central administration apparatus in communication with said memory, and being communicable with said medical devices via a network in which said central administration apparatus functions as a server and the medical devices function as respective clients of the server;
 each medical device being configured, prior to implementing a respective medical task at a respective medical device among said plurality of medical devices, to establish a communication connection via said network between the respective medical device and the central administration apparatus to request a configuration file;
 said central administration apparatus being configured in response to the request, to automatically initiate a search of said memory to select a version of a configuration file in said memory that satisfies criteria that include at least appropriateness of a version of a configuration file for use in performing the respective medical task at the respective medical device, and a current run-time environment of the respective medical task at the respective medical device;
 said central administration apparatus being configured to automatically make a version of a configuration file in said memory, that satisfies said criteria, available, as a selected configuration file, to the respective medical device for check-out;
 the respective medical device being configured to check out the selected file, as a checked-out file, from the central administration apparatus via the communication connection in a form that allows a change in the checked-out file to be made at the respective medical device;
 the respective medical device being configured to complete the respective medical task at the respective medical device and thereafter to return the checked-out file, via the communication connection, to the central administration apparatus as a checked-in file; and
 said central administration apparatus being configured to, upon receipt of each checked-in file at said central administration apparatus, automatically determine whether the checked-in file contains a change made by the respective medical device and, if a change in the checked-in file is detected, to store the checked-in file in said memory as another version of the configuration file, with an indicator of said change that causes said change to be automatically identified and used by said central administration apparatus, in a subsequent search of said memory initiated by a respective medical device, to satisfy said appropriateness in the criteria of said subsequent search.

11. A non-transitory, computer-readable data storage medium encoded with programming instructions for administrating configuration files in a medical facility, said medical facility comprising a plurality of computer-operated medical devices that each operate to perform a respective medical task according to a configuration file, a memory in which a plurality of different configuration files, respectively for different medical devices, are stored, at least some of said configuration files being stored in said memory as different versions of a configuration file, and a central administration apparatus in communication with said memory, and being communicable with said medical devices via a network in which said central administration apparatus functions as a server and the medical devices function as respective clients of the server, said programming instructions being respectively loaded into said central administration apparatus and said plurality of medical devices and causing:
 prior to implementing a respective medical task at a respective medical device among said plurality of medical devices, the respective medical device to establish a communication connection via said network between the respective medical device and the central administration apparatus to request a configuration file;
 said central administration apparatus, upon receipt of the request, to automatically initiate a search of said memory, via said central administration apparatus, to select a version of a configuration file in said memory that satisfies criteria that include at least appropriateness of a version of a configuration file for use in performing the respective medical task at the respective medical device, and a current run-time environment of the respective medical task at the respective medical device;
 said central administration apparatus to automatically make a version of a configuration file in said memory, that satisfies said criteria, available, as a selected configuration file, to the respective medical device for check-out;
 the respective medical device to check out the selected file, as a checked-out file, from the central administration apparatus via the communication connection in a form that allows a change in the checked-out file to be made at the respective medical device;
 after completion of the respective medical task at the respective medical device, the respective medical device to return the checked-out file, via the communication connection, to the central administration apparatus as a checked-in file; and
 said central administration apparatus, upon receipt of each checked-in file at said central administration apparatus, to automatically determine whether the checked-in file contains a change made by the respective medical device and, if a change in the checked-in file is detected, to store the checked-in file in said memory as another version of the configuration file, with an indicator of said change that causes said change to be automatically identified and used by said central administration apparatus, in a subsequent search of said memory initiated by a respective medical device, to satisfy said appropriateness in the criteria of said subsequent search.

* * * * *